United States Patent [19]
Skerritt et al.

[11] Patent Number: 5,541,079
[45] Date of Patent: Jul. 30, 1996

[54] MONOCLONAL AND POLYCLONAL ANTIBODIES AND TEST METHOD FOR DETERMINATION OF ORGANOPHOSPHATES

[76] Inventors: John H. Skerritt; Amanda S. Hill, both of 18 Sunset Avenue, Hornsby Heights NSW 2077; David P. McAdam, 84 Bourne Street, Cook ACT 2614, all of Australia

[21] Appl. No.: 300,931

[22] Filed: Sep. 6, 1994

Related U.S. Application Data

[63] Continuation of Ser. No. 784,398, Dec. 30, 1991, abandoned, which is a continuation of PCT/AU90/00278, Jun. 29, 1990.

[30] Foreign Application Priority Data

Jun. 30, 1989 [AU] Australia .................. PJ5018

[51] Int. Cl.$^6$ .................. G01N 33/53; G01N 33/543
[52] U.S. Cl. .................. 435/7.93; 436/547; 436/548; 530/388.9; 530/389.8
[58] Field of Search .................. 435/7.92, 7.93, 435/240.27, 961; 436/547, 548, 815; 530/388.9, 389.8

[56] References Cited

U.S. PATENT DOCUMENTS 5,128,240  7/1992  Shah .................. 435/7.1

OTHER PUBLICATIONS

Desmarchelier, J. "A Rapid, Colorimetric, Procedure for Determination of Fenitrothion," *Environ. Sci. Health* B16:419–426 (1981).
Kováč, J. and E. Sohler. "Bestimmung von O,O–Dimethyl–O–(3–methyl–4–nitrophenyl)–thiophosphat–Rückständen in Obst und Gemüse nach varngeganener Abtrennung der mitextrahierten Farbstoffe durch Dunnschichtchromatographie," *Fresenius' Z. Anal. Chem.* 208:201–204 (1965).
Dayananda, S. and N. V. Nanda Kumar. "Colorimetric Quantification of Chicken Egg Albumin Cholinesterase Inhibition of Estimation of Fenitrothion and Oxygen Analog," *Journal of Food Science and Technology* 22:107–109 (Mar./Apr. 1985)
Hunter & Lenz, Life Sci. 30 (1982) 355.
Haas & Guardia Proc. Soc. Exp. Biol. Med. 129 (1968) 543.
Ngeh–Ngwainbi et al. Amer. Chem. Soc. 108 (1986) 5444.
Vallejo et al., J. Agric. Food Chem., vol. 30, No. 3, (1982) 572–580.
Centeno et al., Int. Arch. Allergy 37: 1–13 (1970).
Brimfield et al., J. Agric. Food Chem. 1985, 33, 1237–1242.
Hunter et al., FEBS Letters, vol. 149, No. 1, Nov. 1982, pp. 147–151.
Buenafe et al., Molecular Immunology, vol. 24, No. 5, pp. 401–407, 1987.
Sudi et al., W. Kiel. Milchwirtsch. Forschungsber 40 (1988) 179.
Harlow et al *Antibodies A Laboratory Manual* (SH (1988) pp. 72, 139–243, 559, 570–573, 584–582, 591–593.
Padki et al Indian J Med Res 79 Jan. 1984, pp. 137–141.
Ercegovich et al J. Agric. Food Chem. (1981) 29 559–563.
Heldman et al FEBS 180 pp. 243–247 (1985).

*Primary Examiner*—James C. Housel
*Assistant Examiner*—Gary Tanigawa
*Attorney, Agent, or Firm*—Foley & Lardner

[57] ABSTRACT

Monoclonal and polyclonal antibodies and fragments thereof are described which are capable of binding to specific members or groups of O,O-dialkyl-O-(X) phosphorothioate compounds, where X is an aromatic or heterocyclic group or substituted aromatic or substituted heterocyclic group. Specifically, organophosphorus pesticides (e.g. fenitrothion, chloryrifos-methyl, and pirimiphos-methyl) are conjugated to a carrier with a beta-alanine spacer and used as an immunogen for raising antibodies. Hybridoma cell lines, methods for making the antibodies, and assays and kits including the antibodies are also disclosed.

31 Claims, No Drawings

MONOCLONAL AND POLYCLONAL ANTIBODIES AND TEST METHOD FOR DETERMINATION OF ORGANOPHOSPHATES

This application is a continuation of application Ser. No. 07/784,398, filed Dec. 30, 1991, now abandoned (which is a National Stage of PCT/AU90/00278 filed on Jun. 29, 1990).

The present invention relates to a means of generating both polyclonal antibodies and hybridoma cell lines which produce monoclonal antibodies binding to fenitrothion (O,O-dimethyl O-(3-methyl-4-nitrophenyl) phosphorothioate, CAS 122-14-5) and closely related organophosphorus pesticides, such as chlorpyrifos-methyl, chlorpyrifos-ethyl and pirimiphos-methyl, and particularly to a method of detecting fenitrothion and these organophosphorus pesticides in water, foods and agricultural produce (especially grain) using these antibodies. The organophosphorus pesticides are a large class of insecticides which function by inhibition of cholinesterase in the insect neuromuscular junction. Such inhibition produces paralysis, suffocation and eventually death.

As used herein "closely related organophosphates" refers to compounds of the type O,O-dimethyl O-(X) phosphorothioate or O,O- diethyl O-(X) phosphorothioate, where X is an aromatic or heterocyclic group or substituted aromatic or substituted heterocyclic group. Examples include 3-methyl- 4-nitrophenyl, 3,5,6-trichloro-2-pyridyl or 2-diethylamino-6-methylpyrimidin-4-yl.

Fenitrothion is a broad-spectrum insecticide used widely for treatment of crops such as cereals, fruits, vegetables, legumes, cotton, coffee and tea, forest trees and domestic mosquito control. Widespread spraying of fenitrothion has been used for plague locust swarms. Although it is of lower acute mammalian toxicity than many other organophosphorus pesticides, legal maximum residue limits in most food products exist for each of these compounds, for example, those set by the Codex Alimentarius Commission of the Food and Agriculture Organisation and World Health Organisation or those set by the US Environmental Protection Agency under authority of the Federal Food, Drug and Cosmetic Act. Conventional methods for detection or determination of fenitrothion and related organophosphorus pesticides are accurate and precise, but are not well suited to either field analysis of the compound or high-throughput analysis in small laboratories with minimal equipment. Analyses by gas-liquid chromatography (Sissons, D. J., J. Chromatography 47 (1970) 328; Ambrus, A., J. Assoc. Off. Anal. Chem. 64 (1981) 733; Bottomley, D. and Baker, P. G. Analyst 109 (1984) 85) and high-performance liquid chromatography (Funch, F. H. Z. Lebensm. Unters. Forsch. 173 (1981) 95) suffer from high equipment cost, need for skilled operators or analysts and both low sample throughput and relatively long sample analysis time. Removal of interfering components (sample "clean-up") is needed for most chromatographic analyses. Thin-layer chromatography (Bhaskar, S. U. Talanta 29 (1982) 133; Pis'mennaya, M. V. Khim. Sel'sk. Khoz, 18 (1980) 54) does not require high-cost equipment, but is only semi-quantitative and the organophosphorus pesticide present can be difficult to distinguish from related compounds. Enzymic assays for organophosphates based on cholinesterase inhibition are fast and relatively simple, but are not specific for individual organophosphates; in some cases, sensitivity can be insufficient (Dayananda, S. and Kumar, N. V. N., J. Food Sci. Technol. 22 (1985) 107 Goodson, L. H. and Goodman, A., U.S. Pat. No. 4,328,858 (1982)). Field-based tests for spectrophotometric determination of fenitrothion after either derivatization or alkaline hydrolysis to 4-nitro-3-methylphenoxide (Kovac, I. and Sohler, E., Fresenius' Z. Anal. Chem. 208 (1965) 201; Desmarchelier, J. M., J. Environ. Sci. Health, B16 (1981) 419) are either not compound-specific, lack sensitivity or may require extract clean-up followed by use of toxic or corrosive chemicals. Thus, there exists a need for simple, rapid and reliable means of determining fenitrothion and closely related organophosphates. Modern immunoassays, based on either polyclonal or monoclonal antibodies are a useful alternative to conventional chemical and instrumental assays for organophosphorus pesticides. Small organic molecules such as fenitrothion are not by themselves immunogenic, but can be made immunogenic following chemical conjugation to a suitable carrier such as a protein. The site and nature of conjugation and carrier protein can affect the specificity and affinity of antibodies produced, in a manner not fully able to be predicted by those skilled in the art. For example, preparation of reduced parathion (a compound closely related to the hapten used in the present invention) coupled with long bridging groups (glutarimine and diazobenzoic acid) did not yield conjugates producing antisera with useful reaction with parathion (Vallejo, R. D., Bogus, E. R. and Mumma, R. O. J. Agric. Food Chem. 30 (1982) 572).

In recent years, techniques of producing monoclonal antibodies have been developed which make it possible to obtain homogeneous, highly specific antibodies. Generally, such antibodies are produced by immunizing an animal with a protein, obtaining antibody-producing cells from the animal, and fusing the antibody-producing cells with strains of myeloma cells, i.e., tumour cells, to produce hybridomas which are isolated and cultured as monoclones. The monoclonal hybridomas may either be cultured in vitro or may be grown as tumours in a host animal. Since each antibody-producing cell produces a single unique antibody, the monoclonal cultures of hybridomas each produce a homogeneous antibody which may be obtained either from the culture medium of hybridoma cultures grown in vitro or from the cells, ascitic fluid, or serum of a tumour-bearing host animal.

Not all of the hybridoma clones which result from fusing myeloma cells with antibody-producing cells are specific for the desired pesticide (or for functional groups upon the pesticide characteristic of that class of molecules), since many of the hybridomas will make antibodies which the inoculated animal has produced to react with other foreign substances. Even antibodies against the subject antigen will differ from clone to clone, since antibodies produced by different cells may react with different antigenic determinants of the same molecule. From each clone, therefore, it is necessary to obtain the resulting antibody and test its reactivity with the subject pesticides (eg fenitrothion, chlorpyrifos-methyl, chlorpyrifos-ethyl or pirimiphos-methyl) and to test its specificity by determining which particular organophosphorus pesticides it recognizes. Further, only certain antibodies or antisera function in specific immunoassay configurations or formats.

The present invention has very particular and important applications. Firstly, fenitrothion and closely related organophosphates are routinely applied to grain and other produce intended for storage for several months or for export before further processing or consumption. As insect infestation will render the product unsuitable for human consumption or sale, it is important to ensure that application of organophosphorus protectant has been evenly distributed, and in sufficient quantities.

Secondly, it is critical to ensure that levels of fenitrothion and closely related organophosphates in grain and other produce for human consumption do not exceed maximum residue levels (MRL) set by appropriate legislation. For example, the MRL for fenitrothion in wheat grain is 10 ppm, in white flour, 1 ppm and in white bread, 0.2 ppm. The MRL for chlorpyrifos-methyl in wheat grain is 10 ppm, in white flour 2 ppm and in white bread 0.5 ppm.

Thirdly, while reliable methods exist for the specific determination of fenitrothion and closely related organophosphates by chromatographic methods, these methods are not suitable for on-farm or at-market testing, for use by small or less well-equipped food, grain or produce laboratories, or for use in the field for monitoring of environmental pollution of water or soil samples or contamination of animal and fish samples.

The application of the present invention in determining fenitrothion and closely related organophosphates without requirement for chromotographic instrument or expertise, by means of simple antibody-based tests, is therefore a substantial contribution to the art, particularly in the food and environmental analysis fields.

Prior art is evident in the scientific literature on the use of immunochemical methods to detect or to determine organophosphorus cholinesterase inhibitors, including pesticides. These include polyclonal antisera to malathion (Haas, J. H. and Guardia, E. J., Proc. Soc. Exp. Biol. Med. 129 (1968) 546; Centeno, E. R., Johnson, W. J. and Sehon, A. H., Int. Arch. Allergy 37 (1970)) parathion (Ercegovich, C. D., Vallejo, R. P., Gettig, R. R., Woods, L., Bogus, E. R. and Mumma, R. O., J. Agric. Food Chem. 29 (1981) 559; Ngeh-Ngwainbi, J., Foley, P. H., Kuan, S. S. and Guilbault, G. J. Amer. Chem. Soc. 108 (1986) 5444) and paraoxon (Hunter, K. W. and Lenz, D. E., Life Sci. 30 (1982) 355; Lober, M., Krantz, S. and Herrmann, I. Acta. Biol. Med. Get. 41 (1982) 487; Heldman, E., Balan, A., Horowitz, O., Ben-Zion, S. and Torten, M. FEBS Lett. 180 (1985) 243) and monoclonal antibodies to paraoxon (Brimfield, A. A., Lenz, D. E., Graham, C. and Hunter, K. W. J. Agric. Food Chem. 33 (1985) 1237) and soman (Hunter, K. W., Lenz, D. E., Brimfield, A. A. and Naylor, J. A. FEBS Lett. 149 (1982) 147; Buenafe, A. C. and Rittenburg, M. B. Mol. Immunol. 24, (1987) 401). However, cross-reaction of these antibodies with fenitrothion and closely related organophosphates such as chlorpyrifos-methyl, chlorpyrifos-ethyl and pirimiphos-methyl was not normally assessed, and as these antibodies were prepared to other organophosphates they would not be specific for fenitrothion and closely related organophosphates as hereinbefore defined. Immunoassays have also been developed which specifically detect organophosphate pesticides with diethyl thiophosphate esters but these did not detect fenitrothion and chlorpyrifos-methyl (Suedi, J. and Heeschen, W. Kiel. Milchwirtsch. Forschungsber 40 (1988) 179). Antibodies to fenitroxon, the active metabolite of fenitrothion, have been described, (Padki, M. M. and Bhide, M. B., Indian J. Med. Res. 79 (1984) 137) but these have not been used in the determination of organophosphates.

Thus, according to a first aspect, the present invention provides an antibody or fragment thereof, capable of binding to at least one compound from the group comprising O,O-dimethyl O-(3-methyl-4-nitrophenyl) phosphorothioate, O,O-dimethyl O-(3-methyl-4-aminophenyl) phosphorothioate, O,O-dimethyl O-(3-methyl 4-(methylthio)phenyl) phosphorothioate, O,O-dimethyl O-(4-aminosulfonyl)phenyl phosphorothioate, O,O-dimethyl O-(O,O',O'-tetramethyl O,O'-thiodi-p-phenylene-bis(phosphorothioate)) phosphorothioate, O,O-dimethyl O-(3,5,6-trichloro-2-pyridyl) phosphorthioate, O,O-dimethyl O-(2-diethylamino-6-methylpyrimidin-4-yl) phosphorothioate and O,O-diethyl O-(2-diethylamino-6-methylpyrimidin-4-yl) phosphorothioate.

Some of the antibodies and fragments thereof according to the present invention are also capable of binding to at least one other compound of the type $(YO)_2PS-OX$, wherein said X is an aromatic or heterocyclic group or substituted aromatic or substituted heterocyclic group and said Y is a lower alkyl.

The antibodies or fragments thereof, according to the present invention, may be polyclonal, however more preferred are monoclonal antibodies and fragments thereof. The present invention also extends to hybridoma cell lines able to produce such monoclonal antibodies and fragments thereof.

The present invention also provides a novel, generic means of chemically activating an organophosphorus pesticide by means of derivatization through a phosphorus atom by means of a protected ester or acid of a suitable spacer-arm compound. Preferably the spacer is beta-alanine. The acid reactive group on the spacer may be protected with any protective groups which can be removed in non-basic conditions. Suitable protective groups include Trityl (triphenyl methyl), t-pentyl, t-hexyl and trimethyl silyl ethanol, however t-butyl is particularly preferred. The organophosphate conjugate derivatives may be subsequently rendered chemically reactive with carrier macromolecules by mild and facile hydrolysis.

Thus, in a second aspect, the present invention provides a method for producing protected spacer-linked O-mono alkyl-O-(X) phosphorothioates able to be deprotected in non-basic conditions, comprised of, reacting an alkoxy derivative of thiophosphoryl chloride with a protected ester or acid spacer, followed by reaction with a phosphate ester hydrolysis product of a compound of the type $(YO)_2$-PS-OX.

In a still further aspect of the present invention there is provided methods for quantifying fenitrothion or closely related organophosphate particularly in produce or foods, comprising the application of samples or sample extracts thought to contain fenitrothion or related pesticides to a suitable support, applying to said support a solution of suitably labelled antibody specific for fenitrothion or closely related organophosphates, or a solution of suitably labelled fenitrothion or fenitrothion analogue or related O,O-dialkyl-O-phosphorothioate (hapten), and after optionally washing, subjecting the labelled antibody or hapten bound to this solid phase support to an appropriate signal amplification step or other detection procedure.

An appropriate signal amplification step may be an enzyme immunoassay step, where an appropriate enzyme may be coupled to the antibody and subsequently substrate is added to the antigen/enzyme-labelled antibody complex. Alternatively radioimmunoassay, fluorescence immunoassay, chemiluminesence, agglutination or adherence electrochemical or optical methods or combinations thereof may be used as appropriate detection steps.

Suitable solid phase supports may have a variety of configurations and may include tubes, well plates, microplates, elongate sticks or thin strips or beads. The materials that such solid phase surfaces may be formed from include polystyrene or other suitable plastics, nitrocellulose, nylon, polyvinylidene difluoride, glass, silica or other suitable material, such material having been precoated with either polyclonal or monoclonal antibody specific for fenitrothion or another O,O-dialkyl-O-phosphorothioate or a suitable carrier macromolecule substituted with an analogue of fenitrothion or closely related organophosphate.

The hybridoma cell lines according to this invention are preferably produced by the fusion of an antibody producing cell and a myeloma cell derived from a murine species. The antibody producing cells are preferably spleen cells. Any suitable myeloma cell line may be used however it is desirable to use a well characterised cell line of which a number are in common usage.

The testing method according to the present invention does away with the need for sample "clean-up" by solvent extraction, phase transfer or adsorption chromatography (methods commonly used in sample preparation for chromatographic pesticide analysis) is not required. The procedure is adaptable to either rapid (under 15 minute) analysis of individual samples or simultaneous analysis of many dozen samples, does not require expensive automated equipment, and allows such assays to be performed by small laboratories or in field or market situations. Further, the present invention is suitable for raw grain or produce or cooked or processed foods; the fenitrothion or closely related organophosphates may be extracted in a single step. The method of the present invention is simple, inexpensive and reliable and allows either a qualitative or quantitative determination of fenitrothion or closely related organophosphate. Additionally the sensitivity of the test may be readily altered by changing antibody or antigen concentration, hapten substitution ratios or solvent to solid extraction ratios.

The invention is herein further described by way of examples describing preparation of the immunogens, polyclonal antisera, cell-lines and monoclonal antibodies according to the present invention and the use of those antibodies to determine fenitrothion and closely related organophosphates in foodstuffs and agricultural produce such as grain.

Production of immunogen conjugates

O,O-dimethyl-O-(3-methyl-4-aminophenyl) phosphorothioate (I) was converted to the diazonium salt by treatment with sodium nitrite in dilute hydrochloric acid at 0° C., and reaction with either hen egg ovalbumin or keyhole limpet haemocyanin. Alternatively, (I) was treated with methyl adipoyl chloride, the methyl ester hydrolysed and the acid converted to the N-hydroxysuccinimide ester using dicyclohexyldicarboxinimide (DCC), and subsequently reacted with hen egg ovalbumin or chicken serum IgG.

In a more general method for preparation of the immunogens, thiophosphoryl chloride was refluxed in methanol/trichloromethane, then the product reacted under alkaline conditions with t-butyl beta-alanine ester to give the bifunctional reagent (IIa) which was followed by reaction with either 3-methyl-4-nitrophenol (A) or 3,5,6-trichloro-2-pyridinol (B) or 2-diethylamino-4-hydroxy-6-methylpyrimidine (C) in acetonitrile to yield (IIA) or analogous compounds (IIB) or (IIC).

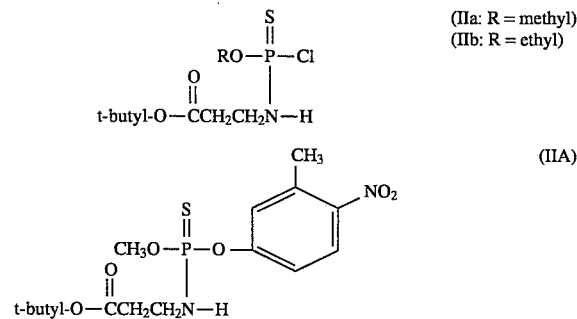

Thiophosphoryl chloride may also be refluxed in ethanol/trichloromethane and then the product reacted as above with t-butyl beta-alanine ester to give (IIb) followed by reaction with, for example, 3,5,6-trichloro-2-pyridinol (B) to yield (IID).

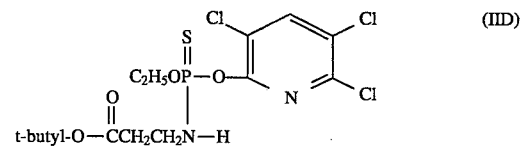

The t-butyl esters (II A-D) are then hydrolyzed and reacted with N-hydroxysuccinimide in dicyclohexyldicarboxinimide (DCC)/methylene chloride to yield III A-D. These compounds (III A-D) were reacted with the various carrier proteins, including chicken IgG, hen egg ovalbumin and keyhole limpet haemocyanin to yield immunogens. The degree of coupling (hapten-to-carrier molar ratio) was between 2 and 50 for each conjugate and could be varied by altering molar ratios of reactants or the reaction conditions.

The derivatization of an organophosphate pesticide by reaction of a beta-alanine derivative with the organophosphate phosphorus for conjugation with a carrier protein for the purpose of preparing antibodies to the organophosphate pesticide, paroxon, is disclosed by Heldman, E. Balan, A. Horowitz, D. Ben-Zion, S. and Torten, M. FEBS Letters, 180 (1985), 243–247. However, these workers derivatized one particular organophosphate pesticide only and used a trimethyl silyl ester of beta-alanine in the nucleophilic substitution reaction on O-(4-nitrophenyl)-O-methyl phosphorochloridate. Such a derivative is unstable to moisture and since it cannot be used as a general method, a new synthesis is required for each organophosphate. By preparing the bifunctional reagent (II), an easier and more useful method of conjugation is obtained, because it may be used for any O,O-diakyl-O-phosphorothioate and the derivatives can be stored for extended periods prior to coupling reactions with macromolecules.

It will be appreciated by those skilled in the art that other conjugation methods, bifunctional reagents and carrier proteins may yield immunogens producing antibodies with reactivity for fenitrothion and closely related organophosphates.

Production of polyclonal antisera and monoclonal antibodies

Individual rabbits (New Zealand White) were immunized with one of the immunogen conjugates. The initial immunization in 50% Freunds complete adjuvant (1000 μg conjugate (half subcutaneous, half intramuscular)) was followed by 500 μg conjugate per rabbit in Freunds incomplete adjuvant, two and four weeks later and at monthly intervals thereafter. Antibodies were harvested from serum using Protein A-Sepharose chromatography.

For preparation of monoclonal antibodies mice (Balb/c) were injected with one of the immunogen conjugates. The initial immunization in 50% Freunds complete adjuvant (400 μg conjugate) was followed by 100 μg conjugate per mouse in Freunds incomplete adjuvant, two and four weeks later. Doses were divided with half given subcutaneously and half intramuscularly. Four to eight weeks later mice were given an intraperitoneal booster injection (900 μg) and the spleens removed for fusion, four days later. Spleen cells were fused with an appropriate mouse myeloma cell line (Sp 2/0, Galfre, G., Howe, S.C., Milstein, D., Butcher, G. W. and Howard, J. C. Nature 266 (1977) 550) using polyethyleneglycol. The details of the fusion protocol and culture techniques have been described elsewhere (Shulman, M., Wilde, C. D. and Kohler, G. Nature 276 (1978) 269). Fused cells (hybridomas) were separated by dilution and antibody-secreting clones were subcloned by limiting dilution. For some subclones, hybridomas were grown as ascites tumours for 10 days in mice.

Preparation of enzyme-labelled fenitrothion

Reduced fenitrothion (O,O-dimethyl-O-( 3-methyl-4-aminophenyl) phosphorothioate) (I) was coupled to the marker enzyme, horseradish peroxidase or its hydrazide derivative perpared according to Gershoni, J. M., Bayer, E. B. and Wilchek, M. *Anal. Biochem.* 146, pp59 (1985), by several means. In one application, methyl adipoyl chloride was coupled to the aromatic amino group of (I), followed by hydrolysis of the methyl ester in aqueous alkaline ethanol. The acid formed was derivatized to the succinimide by treatment with N-hydroxysuccinimide in DCC and methylene chloride. This succinimidyl ester was reacted in a 40 mole excess with horseradish peroxidase at 4° C. for 16 hours.

In some cases, (I) was coupled to bovine serum albumin by this procedure and the conjugate coupled to horseradish peroxidase following Schiff base formation by a method adapted from a published technique (Nakane, P. K. and Kawoi, A. J. Histochem. Cytochem. 22 (1974) 1084).

(I) was also coupled to horseradish peroxidase by means of a beta-alanine spacer-arm as follows. (I) was reacted with the t-butoxy carbonylamide of beta-alanine in the presence of dicyclohexylcarboxinimide. Following deprotection with aqueous trifluroacetic acid and treatment with acidified methanol, the resultant amine (II) was reacted with periodate-treated horseradish peroxidase at pH 9.5 for 4 hours at 20° C. Unreacted aldehyde groups on the enzyme were quenched with ethanolamine. Compounds (III A-D), described hereinbefore derivatized on phosphorus (by reaction with beta alanine t-butyl ester) were also reacted with horseradish peroxidase or its hydrazide derivative. Those skilled in the art will recognise that similar conjugations with other marker enzymes are possible.

RESULTS

Assay Format 1. Enzyme-immunoassay with competition for solid-phase-bound fenitrothion-specific antibody between pesticide present in a sample extract and an enzyme-labelled fenitrothion analogue The solid phase is coated with fenitrothion-specific antibody. For the results listed in Table I, polyclonal IgG antibodies to fenitrothion amine coupled to chicken serum IgG through adipic acyl chloride-6-ethyl ester were used (antibody P1), although similar results may be obtained with monoclonal antibodies prepared to this immunogen and monoclonal and polyclonal antibodies prepared to other immuogens, as described hereinbefore. Preferentially the antibody is coated at 10 µg/ml in 50 mM sodium carbonate buffer, pH9.6. Non-specific binding of immunoreactants is then minimized by treatment with a suitable protein or detergent, for example, 10 mg/mL bovine serum albumin in 50 mM sodium phosphate, pH 7.2–0.9% sodium chloride. The grain or food or other sample, such as soil, to be analyzed is extracted in neat methanol or ethanol, although other polar water-miscible solvents may be used, such as isopropanol, acetonitrile and acetone. Mixtures of water and these solvents may also be used. For water analysis, water samples may be used directly. The grain, food or other extract is diluted five-fold in a protein and detergent-containing buffer (for example 10 mg/mL bovine serum albumin or 1 mg/mL Teleostean fish skin gelatin in 0.05% (v/v) Tween in phosphate-buffered saline) applied to the solid phase and enzyme-labelled reduced fenitrothion (diluted similarly) is added immediately. A fenitrothion standard is prepared in methanol or ethanol and dilutions of this standard assayed simultaneously.

An incubation time of 30 min with reduced fenitrothion (P1), fenitrothion (P2), chlorpyrifos-methyl (P9) or pirimiphos-methyl (P11) conjugated to horseradish peroxidase was used for the results shown in Table 1, together with 10 min chromogenic substrate (2,2'-azino-bis (3-ethyl benzthiazoline-6-sulfonic acid)) incubation time. Using this method with antibody P1, no fenitrothion was detected in wheat grain that was not treated with pesticides, or in wheat containing high levels (7 ppm) of pirimiphos-methyl, chlorpyrifos-methyl or azinphos-methyl (organophosphates) or bioresmethrin (pyrethroid). However, fenitrothion was readily detectable in wheats dosed with differing amounts of fenitrothion used in commercial grain treatment practice. Other fenitrothion-enzyme conjugates hereinbefore described can be used, and the overall assay time can be reduced to 3–10 minutes. The chromogen 3,3',5,5'-tetramethylbenzidine may also be used.

Analysis of fenitrothion by this technique is based on the competition between fenitrothion in the test sample and enzyme-labelled fenitrothion for binding to fenitrothion-specific antibody on the solid phase. There is a decrease in the binding of the enzyme-labelled fenitrothion as the concentration of fenitrothion increases in the test sample; this is manifest in decreasing absorbance of the coloured enzyme product. The concentration of fenitrothion in an unknown sample may be determined by comparing the degree of inhibition of antibody binding caused by the addition of the sample extract with that resulting from the addition of known amounts of fenitrothion. Similar principles apply to detection of other, elated pesticides. For analysis of extracts of most foods, grain, agricultural produce and water, no clean-up of the extracts was necessary.

Specificity properties of the antibodies and some results obtained with grain samples are shown in Tables 1 and 2 respectively. The sensitivities obtained are sufficient for analysis of fenitrothion both at low levels of addition and at levels near or in excess of specified maximum residue levels. In addition, the assay may be used to determine residues of fenitrothion or closely related organophosphates in produce stored for long periods or following processing. The test does not determine 4-nitro-3-methylphenol, a major (insecticidally inactive) breakdown product of fenitrothion, produced during cooking (Snelson, J. T. Grain Protectants, ACIAR (1987) p 164). The assay with antibody P1 for example, is specific for fenitrothion and closely related organophosphates. Dimethyl-o-phosphorothioate esters with 4-substituted phenyl moieties are most active. Most active compounds were substituted at the 3-position on the phenyl moiety. Diethyl-o-phosphorothioates had no significant activity. Other common commercially important organophosphates such as dichlorvos, chlorpyrifos-ethyl, pirimiphos-methyl, azinphos-methyl, dimethoate and malathion were detected extremely weakly or not at all. Carbamate pesticides (eg. carbaryl), organochlorine pesticides (eg. dieldrin) and synthetic pyrethroids (eg. bioresmethrin) were not detected. Parathion-methyl was detected weakly. Thus this assay is functionally specific for fenitrothion. This assay format can also be used with chlorpyrifos-methyl or with pirimiphos specific antibodies prepared as hereinbefore described, to provide assays specific for chlorpyrifos-methyl and for pirimiphos-methyl and pirimiphos-ethyl, using antibodies P9 and P11 respectively (Table 1).

Assay format 2. Enzyme-immunoassay with competition for fenitrothion or closely related organophosphate-specific antibody between pesticide present in a sample extract and solid-phase-bound fenitrothion or closely related pesticide.

The solid phase is coated with a pesticide-macromolecule conjugate. For the results listed in Table 1, the following immunogen conjugates were used: P3 and F2 (IIA coupled to ovalbumin), P3b (IIB coupled to ovalbumin), F4 (IIA coupled to chicken serum IgG). Similar results may be obtained with other conjugates as described hereinbefore. Following pretreatment to minimize non-specific binding of conjugate by treatment with a suitable protein or detergent, the fenitrothion-containing sample to be analyzed is added. The grain, food or other sample may either be extracted in methanol, ethanol or other polar water-miscible solvent as hereinbefore described or otherwise with a volatile organic solvent such as dichloromethane or acetone, solvent removed by evaporation and the residue redissolved in a smaller volume of methanol. The extract or reconstituted residue is diluted in a protein and detergent-containing buffer and applied to the solid phase and antibody specific for fenitrothion and closely related organophosphates added immediately. A fenitrothion standard is prepared in methanol and dilutions of this standard assayed simultaneously. Such antibody may either be enzyme-labelled by direct covalent association or a suitable amplification step used to detect binding of the antibody. Analysis of fenitrothion by this technique is based on the competition between fenitrothion in the test sample and solid-phase-bound fenitrothion, for binding to fenitrothion-specific antibody in solution. There is a decrease in the binding of antibody as the concentration of fenitrothion or of closely related organophosphate increases in the test sample; this is manifest in decreasing absorbance of the coloured enzyme product, in the example provided herein. The concentration of fenitrothion or of closely related organophosphate may be assessed as described in assay format 1. Clean-up of the extracts was not necessary.

An antibody incubation time of 30 minutes was used, together with 20 min (2,2'-azino bis (3-ethylbenzthiazoline-6-sulfonic acid)) substrate incubation time for the example provided. Other fenitrothion-macromolecule conjugates and polyclonal and monoclonal antibodies hereinbefore described can be used, and the overall assay time can be reduced to 5–10 minutes or increased to 18 hours for batchwise analysis of large numbers of (several hundred) samples. In the latter case, sensitivity to fenitrothion or closely related organophosphate is also increased.

Results are shown in Table 1.

Sensitivity can be increased even further by use of volatile organic solvents for extraction of the sample, evaporation of solvent and redissolving the residue in a smaller volume of water miscible organic solvent.

The specificies of these assays can differ from that obtained with Assay format 1. The assay with antibody P3 detects fenitrothion but not amino-fenitrothion (reduced fenitrothion). Methyl-parathion, parathion, and dicapthon are detected with less potency than fenitrothion. Thus, certain dimethyl-o-phosphorothioates with 4-nitrophenyl or 4-methylphenyl groups can be detected but not compounds with larger groups substituted in the 4-position. Related (oxo)-phosphates such as paraoxon and dichlorvos are not detected. Dimethyl-o-phosphorothioate pesticides with other than phenyl substitutions are not detected. Pirimiphos-methyl and azinphos-methyl are not detected. Other pesticides, including a carbamate (carbaryl), an organochlorine (dieldrin) and a pyrethroid (bioresmethrin) were not detected by any antibody shown in Table 1.

Thus the assays detect fenitrothion and closely related organophosphorus pesticides. This assay format can also be used with conjugates of related O,O dialkyl phosphorothioates on the solid phase (IIB, IC, IID) and antibody specific to chlorpyrifos-methyl, chlorpyrifos-ethyl or pirimiphos-methyl in solution, to provide assays for chlorpyrifos-methyl (antibody F7), chlorpyrifos-ethyl or pirimiphos-methyl.

TABLE 1

Reaction of antibodies with Fenitrothion and chlorpyrifos-methyl, pirimiphos-methyl and related compounds[a].

| Compound | | Antibody<br>Assay Format<br>Control Pesticide | P1<br>1<br>FN | P2<br>1<br>FN | P3<br>2<br>FN | P3[b]<br>2<br>FN | F2<br>2<br>FN | F4<br>2<br>FN | P9<br>1<br>CP | F7<br>2<br>CP | P11<br>1<br>PY |
|---|---|---|---|---|---|---|---|---|---|---|---|
| 1. | | | | | | | | | | | |
| | a) | fenitrothion (FN) | 1.0 | 1.0 | 1.0 | 1.0 | 1.0 | 1.0 | — | 0.01 | — |
| | | amino fenitrothion | 2.6 | — | — | — | — | — | — | — | — |
| | | methylparathion | 0.03 | 0.1 | 0.03 | 0.02 | 0.01 | 0.2 | — | 0.005 | — |
| | | fenthion | 0.5 | — | — | — | — | — | — | — | — |
| | | cythioate | 0.2 | — | — | — | — | — | — | — | — |
| | | dicapthon | 0.01 | 0.02 | 0.006 | 0.005 | 0.001 | — | — | 0.01 | — |
| | | temephos | — | — | — | — | — | — | — | — | — |
| | b) | chlorpyrifos-methyl(CP) | — | — | — | — | — | — | 1.0 | 1.0 | — |
| | | pirimiphos-methyl (PY) | — | — | — | — | — | — | — | — | 1.0 |
| 2. | | | | | | | | | | | |
| | a) | parathion | — | 0.02 | 0.01 | 0.02 | — | 0.09 | — | — | — |
| | | fensulfothion | 0.01 | — | — | — | — | 0.02 | — | — | — |
| | | dichlofenthion | — | — | — | — | — | — | — | — | — |
| | b) | chlorpyrifos-ethyl | — | — | — | — | — | — | — | 0.07 | — |
| | | pirimiphos-ethyl | — | — | — | — | — | — | — | — | 2.9 |
| 3. | | | | | | | | | | | |
| | a) | dichlorvos | — | — | — | — | — | — | — | — | — |
| | | paraoxon | — | — | — | — | — | — | — | — | — |
| | b) | azinphos-methyl | — | — | — | — | — | — | — | — | — |

TABLE 1-continued

|   | | | | | | | | | | |
|---|---|---|---|---|---|---|---|---|---|---|
|   | dimethoate | — | — | — | — | — | — | — | — | — |
|   | malathion | — | — | — | — | — | — | — | — | — |
| 4. | | | | | | | | | | |
|   | 3-methyl-4-nitrophenol | — | 0.001 | — | — | — | — | — | — | — |
|   | carbaryl | — | — | — | — | — | — | — | — | — |
|   | dieldrin | — | — | — | — | — | — | — | — | — |
|   | bioresmethrin | — | — | — | — | — | — | — | — | — |

Appendix. Chemical names and relationships of pesticides listed.

COMPOUND

1. Dimethyl-O-phosphorothioates $((CH_3O)_2 PSO-X)$ a) X = substituted phenyl

| | |
|---|---|
| fenitrothion | (X = 3-methyl 4-nitrophenyl) |
| reduced fenitrothion | (X = 3-methyl 4-aminophenyl) |
| methyl-parathion | (X = 4-nitrophenyl) |
| fenthion | (X = 3-methyl4-(methylthio)phenyl) |
| cythioate | (X = 4-(aminosulfonyl)phenyl) |
| dicapthon | (X = 2-chloro-4-nitrophenyl) |
| temephos | (X = 0',0'-dimethyl-0'-thiodi-p-phenylene phosphorothioate) | b) X = other

| | |
|---|---|
| chlorpyrifos-methyl | (X = 3,5,6-trichloro-2-pyridyl) |
| pirimiphos-methyl | (X = 2-diethylamino-6-methylpyrimidin-4-yl) |

2. Diethyl-O-phosphorothioates $((CH_5O)_2 PS-OX)$ a) X = substituted phenyl

| | |
|---|---|
| parathion | (X = 4-nitrophenyl) |
| fensulfothion | (X = 4-methyl sulfinylphenyl) |
| dichlofenthion | (X = 2,4-dichlorophenyl) | b) X = other

| | |
|---|---|
| chlorpyrifos-ethyl | (X = 3,5,6-trichloro-2pyridyl) |
| pirimiphos-ethyl | (X = 2-diethylamino-6-methylpyrimidin-4-yl) |

3. Other organophosphates a) 
| | |
|---|---|
| dichlorvos | (2,2-dichlorovinyl dimethylphosphate) |
| paraoxon | $(C_2H_5O-P-O-4-nitrophenyl)$ | b) Dimethyl Phosphorodithioates $((CH_3O)_2 PS-SX)$

| | |
|---|---|
| azinphos-methyl | (X = 3,4-dihydro-4-oxobenzo [d]-1,2,3-triazinyl-3ylmethyl) |
| dimethoate | (X = S-methyl carbamoylmethyl) |
| malathion | (X = 1,2-di (ethoxycarbonyl)ethyl) |

Footnote to Table 1.
a) Data shown are potencies relative to the control pesticide (determined as relative concentration yielding 50% inhibition of antibody binding). Absolute amounts of control pesticide yielding 50% inhibition of antibody binding in competition ELISA are: P1 (10 ng), P2 (1 ng), P3 (3 ng), P3b (0.5 ng), F2 (3 ng), F4 (9 ng), P9 (0.001 ng), F7 (50 ng), P11 (2 ng).
b) Protein conjugate of chlorpyrifos-methyl coated onto solid phase.
— relative reaction less than 0.0005.

TABLE 2

Determination of fenitrothion in grain samples.

| | | Extraction method (ELISA results, ppm) | |
|---|---|---|---|
| Original application (ppm) | Actual amount[a] (ppm) | Overnight Whole grain | Rapid Ground grain |
| 3 | 2.1 | 2 | 2 |
| 9 | 6.3 | 5 | 6 |
| 14 | 9.8 | 9 | 9 |

[a]Analysis by gas-liquid chromatography. Actual values are lower than original application due to losses on grain during storage. Data are means of 3 experiments, assay format 1, antibody P1.

The method of the present invention can be directly applied to a kit for the detection of said organophosphorus pesticides, especially fenitrothion and closely related organophosphates such as chlorpyrifos-methyl, chlorpyrifos-ethyl and pirimiphos-methyl. In particular, kits may be provided for detecting fenitrothion and closely related organophosphates comprising a packet containing fenitrothion-specific antibody-coated microwell plates coated with antibody specific for fenitrothion or closely related organophosphates or strips or other suitable solid support, a standard solution or solutions or preparation containing a defined amount of fenitrothion or closely related dialkyl-O-phosphorothioate, an enzyme-conjugated derivative of fenitrothion or closely related dialkyl-O-phosphorothioate, an enzyme substrate, washing and colour development stopping solutions, and non-specific binding blocking reagents.

Alternatively, kits may be provided for detecting fenitrothion and closely related organophosphates comprising a packet containing fenitrothion or closely related O,O-dialkyl-O-phosphorthioate derivative-conjugated macromolecule-coated microwell plates or strips or other suitable solid support, a standard solution or solutions or preparation containing a defined amount of fenitrothion or closely related O,O-dialkyl-O-phosphorothioate, antibody to fenitrothion or closely related substrate, washing and colour development stopping solutions, and non-specific binding blocking reagents.

Another alternative, are kits to detect fenitrothion or closely related organophosphate constructed to rely on the principle of agglutination, adherence, fluorescence, visual immunoassay, radioimmunoassay or chemiluminescence.

It will be recognised by persons skilled in the art that numerous variations and modifications may be made to the invention as described above without departing from the spirit or scope of the invention as broadly described.

We claim:

1. A method of producing an antibody or fragment thereof capable of binding with high specificity to a phosphorothioate selected from the group consisting of O,O-dimethyl-O-(3,5,6-trichloro- 2-pyridyl)phosphorothioate, O,O-diethyl-O-(3,5,6-trichloro- 2-pyridyl)phosphorothioate, O,O-dimethyl-O-(2-diethylamino- 6-methylpyrimidin-4-yl)phosphorothioate and O,O-diethyl-O-( 2-diethylamino-6-methylpyrimidin-4-yl)phosphorothioate, comprising the steps of:

immunizing an animal with an immunogen conjugate prepared by the steps of:

(a) reacting a methoxy or ethoxy derivative of thiophosphoryl chloride with a protected ester or acid spacer;

(b) reacting the product of step (a) with 3,5,6-trichloro-2-pyridinol or 2-diethylamino-4-hydroxy-6-methylpyrimidine, thereby forming a protected spacer-linked phosphorothioate;

(c) deprotecting said protected spacer-linked phosphorothioate and linking the resultant deprotected spacer-linked phosphorothioate to an immunogenic macromolecule, thereby forming said immunogen conjugate; and recovering an antibody capable of specifically binding to said phosphorothioate, and optionally fragmenting said antibody and recovering an antigen-binding fragment thereof.

2. The method according to claim 1, wherein said antibody is a monoclonal antibody.

3. The method according to claim 1, wherein said antibody is a polyclonal antibody.

4. A method according to claim 1, wherein said spacer is beta-alanine.

5. A method according to claim 1, wherein said protecting group is selected from the group consisting of t-butyl, t-pentyl, t-hexyl, trimethyl silyl ethanol and triphenyl methyl.

6. An antibody or fragment thereof produced by the method of claim 1.

7. An antibody according to claim 6, wherein said antibody binds with high specificity to O,O-dimethyl-O-(3,5,6-trichloro-2-pyridyl)phosphorothioate and does not bind to O,O-dimethyl-O-( 2-diethylamino-6-methylpyrimidin-4-yl)phosphorothioate and O,O-diethyl-O-(2-diethylamino-6-methylpyrimidin- 4-yl)phosphorothioate.

8. An antibody according to claim 6, wherein said antibody binds with high specificity to O,O-diethyl-O-(3,5,6-trichloro-2-pyridyl)phosphorothioate and does not bind to O,O-dimethyl-O-( 2-diethylamino-6-methylpyrimidin-4-yl)phosphorothioate and O,O-diethyl-O-(2-diethylamino-6-methylpyrimidin- 4-yl)phosphorothioate.

9. An antibody according to claim 6, wherein said antibody binds with high specificity to O,O-dimethyl-O-(2-diethylamino- 6-methylpyrimidin-4-yl)phosphorothioate and does not bind to O,O-dimethyl-O-(3,5,6-trichloro-2-pyridyl)phosphorothioate and O,O-diethyl-O-(3,5,6-trichloro-2-pyridyl)phosphorothioate.

10. An antibody according to claim 6, wherein said antibody binds with high specificity to O,O-diethyl-O-(2-diethylamino- 6-methylpyrimidin-4-yl)phosphorothioate and does not bind to O,O-dimethyl-O-(3,5,6-trichloro-2-pyridyl)phosphorothioate and O,O-diethyl-O-(3,5,6-trichloro-2-pyridyl)phosphorothioate.

11. A method for the quantification or detection of a phosphorothioate selected from the group consisting of O,O-dimethyl-O-(3,5,6-trichloro-2-pyridyl)phosphorothioate, O,O-diethyl-O-( 3,5,6-trichloro-2-pyridyl)phosphorothioate, O,O-dimethyl-O-( 2-diethylamino-6-methylpyrimidin-4-yl)phosphorothioate and O,O-diethyl-O-(2-diethylamino-6-methylpyrimidin-4-yl)phosphorothioate, in a produce, grain, food or environmental sample, comprising the steps of:

(a) contacting said sample with an antibody or fragment thereof according to claim 6, in the presence of a known amount of a labeled conjugate of said phosphorothioate, wherein a label is attached through a carboxylic acid group of an ester or acid spacer on the phosphorothioate group of said labeled conjugate; and (b) determining the binding of said labeled conjugate to said antibody or antibody fragment, wherein said binding is inversely proportional to the amount of said phosphorothioate in said sample.

12. The method according to claim 11, wherein said antibody is a monoclonal antibody.

13. The method according to claim 11, wherein said antibody is a polyclonal antibody.

14. The method according to claim 11, wherein said antibody or fragment thereof is bound to a support.

15. The method according to claim 11, wherein said label is an enzyme.

16. The method according to claim 15, wherein said enzyme is horseradish peroxidase.

17. A method according to claim 11, wherein said phosphorothioate is O,O-dimethyl-O-(3,5,6-trichloro-2-pyridyl)phosphorothioate.

18. A method according to claim 11, wherein said phosphorothioate is O,O-diethyl-O-(3,5,6-trichloro-2-pyridyl)phosphorothioate.

19. A method according to claim 11, wherein said phosphorothioate is O,O-dimethyl-O-(2-diethylamino-6-methylpyrimidin- 4-yl)phosphorothioate.

20. A method according to claim 11, wherein said phosphorothioate is O,O-diethyl-O-(2-diethylamino-6-methylpyrimidin- 4-yl)phosphorothioate.

21. A kit for the quantification or detection of a phosphorothioate selected from the group consisting of O,O-dimethyl-O-(3,5,6-trichloro-2-pyridyl)phosphorothioate, O,O-diethyl-O-(3,5,6-trichloro-2-pyridyl)phosphorothioate, O,O-dimethyl-O-( 2-diethylamino-6-methylpyrimidin-4-yl)phosphorothioate and O,O-diethyl-O-(2-diethylamino-6-methylpyrimidin-4-yl)phosphorothioate, comprising:

(a) an antibody or fragment thereof according to claim 6, and (b) a known amount of a labeled conjugate of said phosphorothioate, wherein a label is attached through a carboxylic acid group of an ester or acid spacer on the phosphorothioate group of said labeled conjugate.

22. The kit according to claim 21, wherein said label is an enzyme.

23. The kit according to claim 22, wherein said enzyme is horseradish peroxidase.

24. A kit as claimed in claim 21, wherein said antibody is a monoclonal antibody.

25. A kit as claimed in claim 21, wherein said antibody is a polyclonal antibody.

26. A kit as claimed in claim 21, wherein said antibody or fragment thereof is bound to a solid support.

27. A kit as claimed in claim 21, further comprising a standard solution or preparation containing a known amount of said phosphorothioate.

28. A kit according to claim 21, wherein said phosphorothioate is O,O-dimethyl-O-(3,5,6-trichloro-2-pyridyl)phosphorothioate.

29. A kit according to claim 21, wherein said phosphorothioate is O,O-diethyl-O-(3,5,6-trichloro-2-pyridyl)phosphorothioate.

30. A kit according to claim 21, wherein said phosphorothioate is O,O-dimethyl-O-(2-diethylamino-6-methylpyrimidin-4-yl)phosphorothioate.

31. A kit according to claim 21, wherein said phosphorothioate is O,O-diethyl-O-(2-diethylamino-6-methylpyrimidin-4-yl)phosphorothioate.

* * * * *